US011361193B2

(12) United States Patent
Tian et al.

(10) Patent No.: US 11,361,193 B2
(45) Date of Patent: Jun. 14, 2022

(54) AUTOMATIC IDENTIFICATION METHOD AND SYSTEM FOR DIFFERENT TYPES OF PORES OF MUD SHALE

(71) Applicant: Northeast Petroleum University, Heilongjiang (CN)

(72) Inventors: Shansi Tian, Heilongjiang (CN); Bo Liu, Heilongjiang (CN); Fang Zeng, Heilongjiang (CN); Xiaofei Fu, Heilongjiang (CN); Zhiwei Hu, Heilongjiang (CN); Ya'ao Chi, Heilongjiang (CN); Haiyang Yan, Heilongjiang (CN)

(73) Assignee: Northeast Petroleum University, Heilongjiang (CN)

( * ) Notice: Subject to any disclaimer, the term of this patent is extended or adjusted under 35 U.S.C. 154(b) by 115 days.

(21) Appl. No.: 16/897,952

(22) Filed: Jun. 10, 2020

(65) Prior Publication Data
US 2020/0387759 A1     Dec. 10, 2020

(30) Foreign Application Priority Data

Jun. 10, 2019    (CN) .......................... 201910497324.3

(51) Int. Cl.
*G06K 9/00*       (2022.01)
*G06K 9/62*       (2022.01)
(Continued)

(52) U.S. Cl.
CPC .............. *G06K 9/6267* (2013.01); *G06T 3/40* (2013.01); *G06T 5/50* (2013.01); *G06T 7/13* (2017.01);
(Continued)

(58) Field of Classification Search
CPC ................................. G06T 7/13; G06K 9/6267
See application file for complete search history.

(56) References Cited

FOREIGN PATENT DOCUMENTS

| CN | 105352873 A | * | 2/2016 |
| CN | 109269953 A | * | 1/2019 |
| CN | 109285137 A | * | 1/2019 |

OTHER PUBLICATIONS

Li, Yifan, et al. "Pore characterization and shale facies analysis of the Ordovician-Silurian transition of northern Guizhou, South China: the controls of shale facies on pore distribution." Marine and Petroleum Geology 92 (2018): 697-718. (Year: 2018).*

(Continued)

*Primary Examiner* — Claire X Wang
*Assistant Examiner* — Denise G Alfonso
(74) *Attorney, Agent, or Firm* — Renner, Otto, Boisselle & Sklar, LLP

(57) ABSTRACT

A method for identifying mineral pore types in mud shale includes: determining an inorganic mineral pore image and a kerogen region image of a mud shale Scanning Electron Microscopy (SEM) gray-scale image; performing an expansion operation on the inorganic mineral pore image to obtain an expanded inorganic mineral pore image; comparing the inorganic mineral pore image with the expanded inorganic mineral pore image, and determining an extra region in the expanded inorganic mineral pore image as an expansion region; collecting statistics about the number of pixel points of a siliceous mineral, a calcareous mineral, and a clay mineral; calculating the proportion of each mineral according to the number of pixel points of the minerals; drawing a mineral pore triangular image chart according to the proportions of minerals; and determining the mineral type corresponding to the pores in the inorganic mineral pore image according to the mineral pore triangular image chart.

9 Claims, 9 Drawing Sheets

(51) Int. Cl.
*G06T 7/13* (2017.01)
*G06T 7/70* (2017.01)
*G06T 3/40* (2006.01)
*G06T 5/50* (2006.01)
*G06T 11/20* (2006.01)

(52) U.S. Cl.
CPC .............. *G06T 7/70* (2017.01); *G06T 11/206* (2013.01); *G06T 2207/10061* (2013.01); *G06T 2207/20221* (2013.01)

(56) References Cited

OTHER PUBLICATIONS

Liu, Xuefeng, et al. "Pore-scale characterization of tight sandstone in Yanchang Formation Ordos Basin China using micro-CT and SEM imaging from nm-to cm-scale." Fuel 209 (2017): 254-264. (Year: 2017).*

* cited by examiner (a)　　　　　　　　　　　　(b)

(a)                                  (b)

(a) (b) (c)

AUTOMATIC IDENTIFICATION METHOD AND SYSTEM FOR DIFFERENT TYPES OF PORES OF MUD SHALE

TECHNICAL FIELD

The present invention relates to the technical field of mineral pore identification, and in particular, to an automatic identification method and system for different types of pores of mud shale.

BACKGROUND

Scanning Electron Microscopy (SEM) is a technique for scanning the surface of a sample with high-energy electrons, and can effectively reflect the morphology features of the surface of the sample. The resolution of secondary electrons is generally 5-10 nm. In a region (such as pores) below the surface, the brightness is darker than that of the edge, and charges are accumulated at the edge, which is bright and forms a circle of bright edges. The conventional pore extraction mode is to extract pores to some extent by an artificial hand-painting method, a threshold method, an edge extraction method, and a watershed method.

The results of the artificial hand-painting method vary greatly depending on the geological experience of operators, and there are many small pores in the shale. There are thousands or even tens of thousands of tiny pores in a shale SEM picture, and the workload is huge (dozens or even thousands of SEM pictures can be consecutively photographed), which is time-consuming, and it is easy for the operator to ignore some tiny pores in the hand-painting process. This method is not easy to process a large number of pictures, and is widely used in qualitative or semi-quantitative shale pore evaluation.

The threshold method is a method of dividing a mud shale SEM gray-scale image into a pore region and a background region by using a gray-scale value, because the SEM is dark in the pore region. Therefore, the region where the gray-scale level is lower than a threshold can be defined as the pore, and the region where the gray-scale level is higher than the threshold can be defined as the background. The threshold method is widely used in the processing of SEM because of its simple operation. However, due to the presence of kerogen and dark minerals in the shale, it is easy to identify the kerogen and dark mineral regions as pores to cause errors. Moreover, some shallower large holes have higher internal brightness and a brighter overall color. The large holes with uneven interior have uneven brightness, and it is easy to ignore these bright regions to cause errors. There are two types of threshold methods: an artificial threshold method and an automatic threshold method. The artificial threshold method has the same problem as the artificial hand-painting method: the processing result varies with each individual due to different geological experience of the operators. However, the automatic threshold method does not have this problem. Anyone can obtain the same processing result as long as the automatic threshold method is determined. However, there are various automatic threshold methods at present, but most of them are applied to materials, biological or sandstone and carbonate reservoir samples, and there is no automatic threshold extraction method special for shale samples.

The edge extraction method is a method of first differentially processing a picture, finding a boundary line with sharp changes in light and dark, and extracting the boundary line. If the edge extraction method is applied to the pore extraction process, it is also necessary to fill the extracted boundaries. The edge extraction method can effectively extract the edges of the pores. However, in the process of processing large-area pictures, the uneven surface (edge angle) of the sample and the edges of the contaminants caused by the edge of the kerogen, the edge of the mineral, and the sample pretreatment process will be extracted, resulting in a lot of errors. Moreover, during the extraction of shallow holes and inclined angular pores, the edges may not be fully filled, and the pores may not be filled during the filling of the pores, resulting in errors.

The watershed method is similar to the edge extraction method in that the picture is first subjected to differential processing, but the watershed method then finds the regions lower than a certain value, divides the regions into smaller regions, and identifies the different regions as pores. However, the watershed method and the edge extraction method have similar problems. The kerogen, minerals, pretreatment, and pollutants would cause a lot of errors. Moreover, the watershed method divides the large holes of different internal roughness into different small pores, which causes a lot of errors.

The foregoing method can only identify the pores. In order to identify the pores as organic pores or inorganic pores, the Energy Disperse Spectroscopy (EDS) spectrum is generally obtained by using the EDS, and different mineral and kerogen distribution images and pore images obtained by the EDS spectrum are superposed to determine the organic pores and inorganic pores. The method is cumbersome and the resolution of the mineral and kerogen distribution images obtained by the EDS is low, and the accuracy of an identification result is low.

SUMMARY

On this basis, it is necessary to provide an automatic identification method and system for different types of pores of mud shale, which can not only improve the identification accuracy of mineral pore identification, but also quantitatively identify which minerals control the pores.

To achieve the above purpose, the present invention provides the following technical solutions.

An automatic identification method for different types of pores of mud shale includes:

obtaining a mud shale Scanning Electron Microscopy (SEM) grayscale image;

determining an inorganic mineral pore image and a kerogen region image of the mud shale SEM grayscale image;

performing an expansion operation on the inorganic mineral pore image to obtain an expanded inorganic mineral pore image;

comparing the inorganic mineral pore image with the expanded inorganic mineral pore image, and determining an extra region in the expanded inorganic mineral pore image as an expansion region;

collecting statistics about the number of pixel points of a siliceous mineral, the number of pixel points of a calcareous mineral, and the number of pixel points of a clay mineral in a corresponding region of expansion, the corresponding region of expansion being a region in a resolution-calibrated energy spectrum mineral distribution image corresponding to the expansion region;

calculating the proportion of the siliceous mineral, the proportion of the calcareous mineral, and the proportion of the clay mineral according to the number of pixel points of the siliceous mineral, the number of pixel points of the calcareous mineral, and the number of pixel points of the clay mineral;

drawing a mineral pore triangular image chart according to the proportion of the siliceous mineral, the proportion of the calcareous mineral, and the proportion of the clay mineral, the mineral pore triangular image chart being formed by using the siliceous mineral, the calcareous mineral, and the clay mineral as three end members, and connecting every two of the end members; and determining the mineral type corresponding to the pores in the inorganic mineral pore image according to the mineral pore triangular image chart.

Optionally, the determining an inorganic mineral pore image and a kerogen region image of the mud shale SEM gray-scale image specifically includes:

collecting statistics about the number of pixel points of each gray-scale value in the mud shale SEM gray-scale image, and obtaining a relationship curve of the number of pixel points and the grayscale value;

determining a gray-scale value corresponding to the highest point of an organic matter peak, a gray-scale value corresponding to the highest point of a main mineral peak, a gray-scale value corresponding to the highest point of a bright mineral peak, and peak widths in the relationship curve, the peak widths of the organic matter peak, the main mineral peak and the bright mineral peak being the same;

calculating a first pore gray-scale cutoff value, a kerogen gray-scale cutoff value, and a bright mineral gray-scale cutoff value by using the gray-scale value corresponding to the highest point of the organic matter peak, the gray-scale value corresponding to the highest point of the main mineral peak, the gray-scale value corresponding to the highest point of the bright mineral peak, and the peak widths;

using the first pore gray-scale cutoff value, the kerogen gray-scale cutoff value, and the bright mineral gray-scale cutoff value to respectively perform threshold segmentation on the mud shale SEM gray-scale image to obtain an initial pore image, an initial kerogen pore image, and a bright mineral image;

distinguishing whether kerogen is present in the initial kerogen pore image according to the initial pore image to obtain an inorganic mineral pore image and an initial kerogen region image; and superimposing the initial kerogen region image with the bright mineral image, and removing the corresponding bright mineral in the initial kerogen region image to obtain a kerogen region image.

Optionally, after the determining an inorganic mineral pore image and a kerogen region image of the mud shale SEM gray-scale image, the method further comprises:

determining a calibration image according to the kerogen region image and a mud shale edge extraction image, the mud shale edge extraction image being obtained by performing edge extraction on the mud shale SEM grayscale image;

performing image segmentation on the mud shale SEM gray-scale image according to a preset threshold to obtain a first pore image; and determining an organic pore image according to the kerogen region image, the first pore image, and the orientation image.

Optionally, the method for determining a resolution-calibrated energy spectrum mineral distribution image comprises:

obtaining an energy spectrum mineral distribution image corresponding to the mud shale SEM gray-scale image, the energy spectrum mineral distribution image being obtained by using an energy disperse spectroscopy;

determining three characteristic mineral regions of the mud shale SEM gray-scale image and corresponding regions of each of the characteristic mineral regions in the energy spectrum mineral distribution image;

calculating a centroid of each of the characteristic mineral regions and a corresponding centroid of each of the corresponding regions, and calibrating the size of the energy spectrum mineral distribution image according to the centroid and the corresponding centroid, to obtain a size-calibrated mineral distribution image;

performing corrosion image processing on each type of mineral particles in the size-calibrated mineral distribution image to obtain an image of the corroded particles;

using the image of the corroded particle as a foreground color and the inorganic mineral pore image and the kerogen region image as background colors, segmenting the mud shale SEM gray-scale image by using a watershed algorithm to obtain a segmented mud shale SEM gray-scale image, the segmented mud shale SEM gray-scale image having a plurality of independent regions;

superimposing the segmented mud shale SEM gray-scale image with the size-calibrated energy spectrum mineral distribution image, and collecting statistics about the number of pixel points of all different mineral types in each of the independent regions;

determining the mineral type having the maximum number of pixel points in each of the independent regions as a mineral type corresponding to the independent region; and performing resolution calibration on the size-calibrated energy spectrum mineral distribution image according to all the independent regions with the mineral type determined, to obtain a resolution-calibrated energy spectrum mineral distribution image.

Optionally, the calculating a centroid of each of the characteristic mineral regions and a corresponding centroid of each of the corresponding regions, and calibrating the size of the energy spectrum mineral distribution image according to the centroid and the corresponding centroid, to obtain a size-calibrated mineral distribution image specifically comprises:

calculating a first centroid, a second centroid, a third centroid, a first corresponding centroid, a second corresponding centroid, and a third corresponding centroid, wherein the first centroid is a centroid of a first characteristic mineral region, the second centroid is a centroid of a second characteristic mineral region, the third centroid is a centroid of a third characteristic mineral region, the first corresponding centroid is a centroid of a region corresponding to the first characteristic mineral region, the second corresponding centroid is a centroid of a region corresponding to the second characteristic mineral region, and the third corresponding centroid is a centroid of a region corresponding to the third characteristic mineral region;

calculating a first triangle centroid and a second triangle centroid, wherein the first triangle centroid is a centroid of a triangle formed by the first centroid, the second centroid, and the third centroid, and the second triangle centroid is a centroid of a triangle formed by the first corresponding centroid, the second corresponding centroid, and the third corresponding centroid;

calculating a first slope, a first vertical distance, and a first horizontal distance according to the first centroid, the second centroid, the third centroid, and the first triangle centroid, wherein the first slope is a slope of a connecting line between the first triangle centroid and the first centroid, the first vertical distance is a vertical distance from the first triangle centroid to the first centroid, and the first horizontal distance is a horizontal distance from the second centroid to the third centroid;

calculating a second slope, a second vertical distance, and a second horizontal distance according to the first corresponding centroid, the second corresponding centroid, the third corresponding centroid, and the second triangle centroid, wherein the second slope is a slope of a connecting line between the second triangle centroid and the first corresponding centroid, the second vertical distance is a vertical distance from the second triangle centroid to the first corresponding centroid, and the second horizontal distance is a horizontal distance from the second corresponding centroid to the third corresponding centroid;

rotating the energy spectrum mineral distribution image such that a second slope corresponding to the energy spectrum mineral distribution image is converted into the first slope to obtain a rotated energy spectrum mineral distribution image;

enlarging the rotated energy spectrum mineral distribution image m times in the X-axis direction and n times in the Y-axis direction to obtain an enlarged energy spectrum mineral distribution image, wherein m is a ratio of the first horizontal distance to the second horizontal distance, and n is a ratio of the first vertical distance to the second vertical distance; and superimposing the enlarged energy spectrum mineral distribution image with the mud shale SEM gray-scale image, retaining an overlapped region of the enlarged energy spectrum mineral distribution image with the mud shale SEM gray-scale image, and determining the overlapped region as a size-calibrated mineral distribution image.

Optionally, the determining a gray-scale value corresponding to the highest point of an organic matter peak, a gray-scale value corresponding to the highest point of a main mineral peak, a gray-scale value corresponding to the highest point of a bright mineral peak, and peak widths in the relationship curve specifically comprises:

fitting the relationship curve by using a Gaussian peak-differentiating and fitting method to obtain a fitting curve;

determining an organic matter peak, a main mineral peak, and a bright mineral peak according to the fitting curve, the main mineral peak being a quartz-feldspar-calcite mineral peak; and determining a gray-scale value corresponding to the highest point of the organic matter peak, a gray-scale value corresponding to the highest point of the main mineral peak, a gray-scale value corresponding to the bright mineral peak, and peak widths, the peak widths of the organic matter peak, the main mineral peak, and the bright mineral peak being the same.

Optionally, the distinguishing whether kerogen is present in the initial kerogen pore image according to the initial pore image to obtain an inorganic mineral pore image and an initial kerogen region image specifically comprises:

superimposing the initial pore image and the initial kerogen pore image, and collecting statistics about a first parameter corresponding to each isolated communication region in the initial kerogen pore image and a second parameter corresponding to each pore in the initial pore image, the first parameter comprising a sum of an inner circumference and an outer circumference of the isolated communication region, the area, a long axis value, and a short axis value; and the second parameter being the area of the pores;

determining the area of the maximum pore in the initial pore image according to the second parameter;

establishing a kerogen region discriminant function according to the first parameter and the area of the maximum pore;

distinguishing whether kerogen is present in the initial kerogen pore image by using the kerogen region discriminant function to obtain an inorganic mineral pore image and a kerogen region; and filling the kerogen region to obtain an initial kerogen region image.

Optionally, the determining a calibration image according to the kerogen region image and a mud shale edge extraction image specifically comprises:

using a Sobel operator, a Prewitt operator, a Roberts operator, and a Canny operator to perform edge extraction on the mud shale SEM gray-scale image respectively to obtain a first operator edge image, a second operator edge image, a third operator edge image, and a fourth operator edge image;

combining the first operator edge image, the second operator edge image, the third operator edge image, and the fourth operator edge image to obtain a mud shale edge extraction image; and combining the kerogen region image with the mud shale edge extraction image, and deleting the edge other than the corresponding kerogen region image in the mud shale edge extraction image to obtain a calibration image.

Optionally, the determining an organic pore image according to the kerogen region image, the first pore image, and the calibration image specifically comprises:

superimposing the first pore image and the kerogen region image, and deleting pores other than the corresponding kerogen region image in the first pore image to obtain a second pore image;

comparing the second pore image with the calibration image to determine a pore image at an optimal threshold;

performing inner filling on edges in the calibration image to obtain a filled calibration image; and combining the filled calibration image with the pore image at the optimal threshold to obtain an organic pore image.

An automatic identification system for different types of pores of mud shale includes:

an image obtaining module configured to obtain a mud shale Scanning Electron Microscopy (SEM) grayscale image;

a first determining module configured to determine an inorganic mineral pore image and a kerogen region image of the mud shale SEM grayscale image;

an expansion module configured to perform an expansion operation on the inorganic mineral pore image to obtain an expanded inorganic mineral pore image;

a second determining module configured to compare the inorganic mineral pore image with the expanded inorganic mineral pore image, and determine an extra region in the expanded inorganic mineral pore image as an expansion region;

a statistics module configured to collect statistics about the number of pixel points of a siliceous mineral, the number of pixel points of a calcareous mineral, and the number of pixel points of a clay mineral in a corresponding region of expansion, the corresponding region of expansion being a region in a resolution-calibrated energy spectrum mineral distribution image corresponding to the expansion region;

a proportion calculating module configured to calculate the proportion of the siliceous mineral, the proportion of the calcareous mineral, and the proportion of the clay mineral according to the number of pixel points of the siliceous mineral, the number of pixel points of the calcareous mineral, and the number of pixel points of the clay mineral;

a chart drawing module configured to draw a mineral pore triangular image chart according to the proportion of the siliceous mineral, the proportion of the calcareous mineral, and the proportion of the clay mineral, the mineral pore triangular image chart being formed by using the siliceous mineral, the calcareous mineral, and the clay mineral as three end members, and connecting every two of the end members; and a pore identification module configured to determine the mineral type corresponding to the pores in the inorganic mineral pore image according to the mineral pore triangular image chart.

Compared with the prior art, beneficial effects of the present invention lie in:

The present invention provides an automatic identification method and system for different types of pores of mud shale. The method comprises: determining an inorganic mineral pore image and a kerogen region image of a mud shale SEM gray-scale image; performing an expansion operation on the inorganic mineral pore image to obtain an expanded inorganic mineral pore image; comparing the inorganic mineral pore image with the expanded inorganic mineral pore image, and determining an extra region in the expanded inorganic mineral pore image as an expansion region; collecting statistics about the number of pixel points of a siliceous mineral, a calcareous mineral and a clay mineral; calculating the proportion of the siliceous mineral, the proportion of the calcareous mineral and the proportion of the clay mineral according to the number of pixel points of the minerals; drawing a mineral pore triangular image chart according to the proportions of minerals; and determining the mineral type corresponding to the pores in the inorganic mineral pore image according to the mineral pore triangular image chart. The present invention can quantitatively identify which minerals control the pores, and realize the identification of the mineral pores by using a mud shale SEM gray-scale image-based method. Compared with the method of identifying organic pores and inorganic pores based on an EDS spectrum, the present invention can improve the recognition accuracy of mineral pore identification.

BRIEF DESCRIPTION OF THE DRAWINGS

To describe the technical solutions in the embodiments of the present invention or in the prior art more clearly, the following briefly introduces the accompanying drawings required for describing the embodiments. Apparently, the accompanying drawings in the following description show merely some embodiments of the present invention, and a person of ordinary skill in the art may still derive other drawings from these accompanying drawings without creative efforts.

DETAILED DESCRIPTION

The following clearly and completely describes the technical solutions in the embodiments of the present invention with reference to the accompanying drawings in the embodiments of the present invention. Apparently, the described embodiments are merely a part rather than all of the embodiments of the present invention. All other embodiments obtained by a person of ordinary skill in the art based on the embodiments of the present invention without creative efforts shall fall within the protection scope of the present invention.

To make objectives, features, and advantages of the present invention more comprehensible, the following describes the present invention in more detail with reference to accompanying drawings and specific implementations.

Embodiment 1

Figure 1:
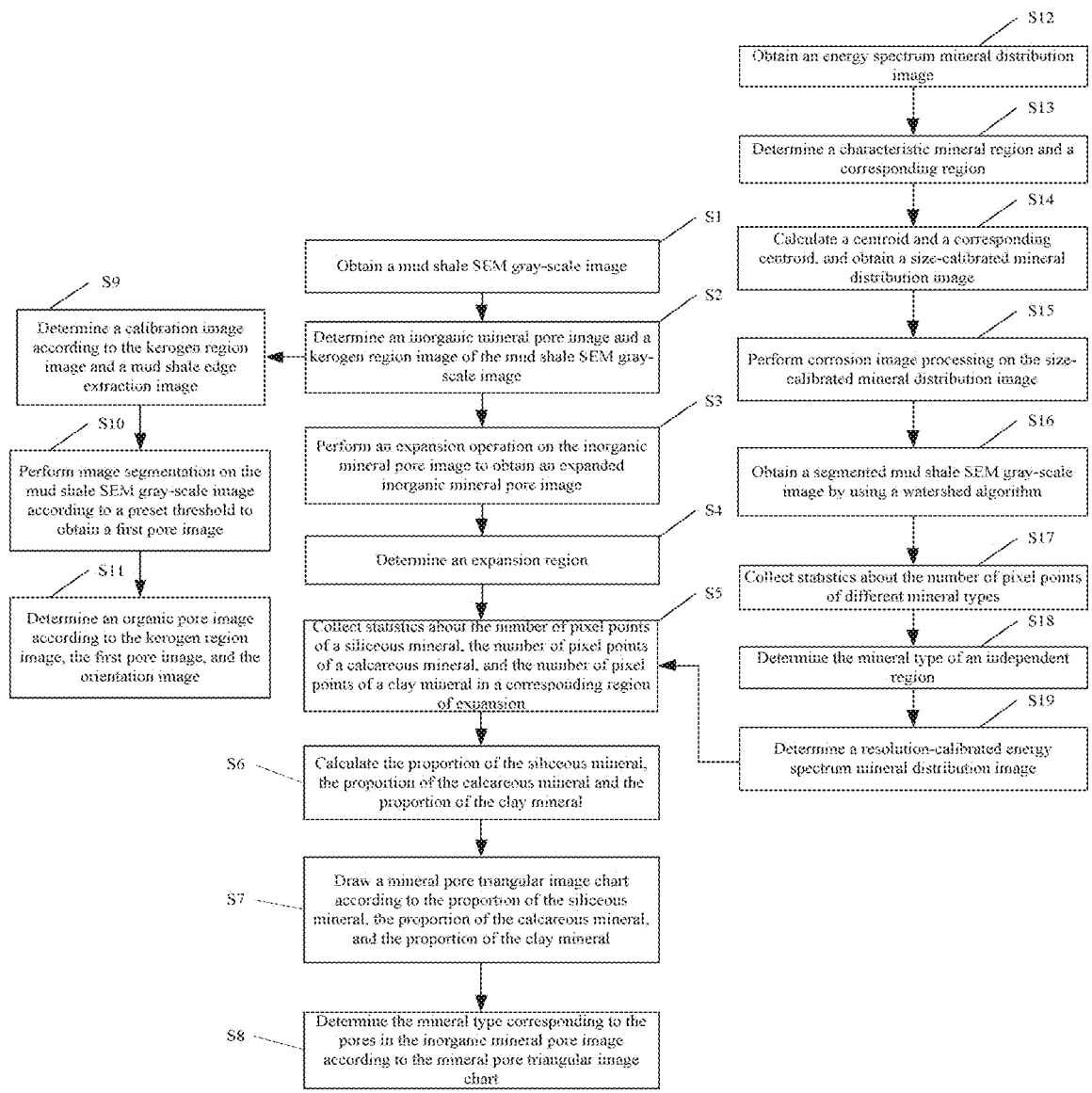
FIG. 1 is a flowchart of an automatic identification method for different types of pores of mud shale according to Embodiment 1 of the present invention.

FIG. 1 is a flowchart of an automatic identification method for different types of pores of mud shale according to Embodiment 1 of the present invention.

Referring to FIG. 1, in this embodiment, an automatic identification method for different types of pores of mud shale includes:

Step S1: a mud shale SEM gray-scale image is obtained.

Step S2: an inorganic mineral pore image and a kerogen region image of the mud shale SEM gray-scale image are determined.

Step S2 specifically includes:

1) The number of pixel points of each gray-scale value in the mud shale SEM gray-scale image is counted, and a relationship curve of the number of pixel points and the gray-scale value is obtained.

2) A gray-scale value corresponding to the highest point of an organic matter peak, a gray-scale value corresponding to the highest point of a main mineral peak, a gray-scale value corresponding to the highest point of a bright mineral peak, and peak widths in the relationship curve are determined. The step is specifically as follows:

The relationship curve is fit by using a Gaussian peak-differentiating and fitting method to obtain a fitting curve; an organic matter peak, a main mineral peak, and a bright mineral peak are determined according to the fitting curve, the main mineral peak being a quartz-feldspar-calcite mineral peak, and the bright mineral peak being a pyrite-apatite-rutile mineral peak; and a gray-scale value corresponding to the highest point of the organic matter peak, a gray-scale value corresponding to the highest point of the main mineral peak, a gray-scale value corresponding to the highest point of the bright mineral peak, and peak widths are determined, the peak widths of the organic matter peak, the main mineral peak and the bright mineral peak being the same.

3) A first pore gray-scale cutoff value, a kerogen gray-scale cutoff value, and a bright mineral gray-scale cutoff value are calculated by using the gray-scale value corresponding to the highest point of the organic matter peak, the gray-scale value corresponding to the highest point of the main mineral peak, the gray-scale value corresponding to the highest point of the bright mineral peak, and the peak widths.

4) The first pore gray-scale cutoff value, the kerogen gray-scale cutoff value, and the bright mineral gray-scale cutoff value are used to respectively perform threshold segmentation on the mud shale SEM gray-scale image to obtain an initial pore image, an initial kerogen pore image, and a bright mineral image.

5) Whether kerogen is present in the initial kerogen pore image is distinguished according to the initial pore image to obtain an inorganic mineral pore image and an initial kerogen region image. The step is specifically as follows:

The step specifically includes the following sub-steps:

51) The initial pore image and the initial kerogen pore image are superimposed, and a first parameter corresponding to each isolated communication region in the initial kerogen pore image and a second parameter corresponding to each pore in the initial pore image are counted, where the first parameter comprises a sum of an inner circumference and an outer circumference of the isolated communication region, the area, a long axis value, and a short axis value; and the second parameter is the area of the pores.

52) The area of the maximum pore in the initial pore image is determined according to the second parameter.

53) A kerogen region discriminant function is established according to the first parameter and the area of the maximum pore.

54) Whether kerogen is present in the initial kerogen pore image is distinguished by using the kerogen region discriminant function to obtain an inorganic mineral pore image and a kerogen region.

55) The kerogen region is filled to obtain an initial kerogen region image.

6) The initial kerogen region image is superimposed with the bright mineral image, and the corresponding bright mineral in the initial kerogen region image is removed to obtain a kerogen region image.

Step S3: an expansion operation is performed on the inorganic mineral pore image to obtain an expanded inorganic mineral pore image.

Step S4: an expansion region is determined. Specifically, the inorganic mineral pore image is compared with the expanded inorganic mineral pore image, and an extra region in the expanded inorganic mineral pore image is determined as an expansion region.

Step S5: the number of pixel points of a siliceous mineral, the number of pixel points of a calcareous mineral, and the number of pixel points of a clay mineral in a corresponding region of expansion are counted. The corresponding region of expansion is a region in a resolution-calibrated energy spectrum mineral distribution image corresponding to the expansion region. The siliceous mineral includes quartz, albite, and potassium feldspar. The calcareous mineral includes calcite, dolomite and apatite. The clay mineral includes illite/smectite mixed layer, illite and chlorite.

Step S6: the proportion of the siliceous mineral, the proportion of the calcareous mineral and the proportion of the clay mineral are calculated. Specifically, the proportion of the siliceous mineral, the proportion of the calcareous mineral, and the proportion of the clay mineral are calculated according to the number of pixel points of the siliceous mineral, the number of pixel points of the calcareous mineral, and the number of pixel points of the clay mineral.

Step S7: a mineral pore triangular image chart is drawn according to the proportion of the siliceous mineral, the proportion of the calcareous mineral, and the proportion of the clay mineral.

The mineral pore triangular image chart is formed by using the siliceous mineral, the calcareous mineral, and the clay mineral as three end members, and connecting every two of the end members.

Step S8: the mineral type corresponding to the pores in the inorganic mineral pore image is determined according to the mineral pore triangular image chart.

As an alternative implementation, after step S2, the method further includes:

Step S9: a calibration image is determined according to the kerogen region image and a mud shale edge extraction image. The mud shale edge extraction image is obtained by performing edge extraction on the mud shale SEM gray-scale image.

Step S9 specifically includes:

1) A Sobel operator, a Prewitt operator, a Roberts operator, and a Canny operator are adopted to perform edge extraction on the mud shale SEM gray-scale image respectively to obtain a first operator edge image, a second operator edge image, a third operator edge image, and a fourth operator edge image.

2) The first operator edge image, the second operator edge image, the third operator edge image, and the fourth operator edge image are combined to obtain a mud shale edge extraction image.

3) The kerogen region image is combined with the mud shale edge extraction image, and the edge other than the corresponding kerogen region image in the mud shale edge extraction image is deleted to obtain a calibration image.

Step S10: image segmentation is performed on the mud shale SEM gray-scale image according to a preset threshold to obtain a first pore image.

Step S11: an organic pore image is determined according to the kerogen region image, the first pore image, and the orientation image.

Step S11 specifically includes:

1) The first pore image and the kerogen region image are superimposed, and pores other than the corresponding kerogen region image in the first pore image are deleted to obtain a second pore image.

2) The second pore image is compared with the calibration image to determine a pore image at an optimal threshold.

3) Inner filling is performed on edges in the calibration image to obtain a filled calibration image.

4) The filled calibration image is combined with the pore image at the optimal threshold to obtain an organic pore image.

As an alternative implementation, the method for determining a resolution-calibrated energy spectrum mineral distribution image includes:

Step S12: an energy spectrum mineral distribution image is obtained. Specifically, an energy spectrum mineral distribution image corresponding to the mud shale SEM gray-scale image is obtained, and the energy spectrum mineral distribution image is obtained by using an EDS.

Step S13: a characteristic mineral region and a corresponding region are determined. Specifically, three characteristic mineral regions of the mud shale SEM gray-scale image and corresponding regions of each of the characteristic mineral regions in the energy spectrum mineral distribution image are determined.

Step S14: a centroid and a corresponding centroid are calculated, and a size-calibrated mineral distribution image is obtained. Specifically, a centroid of each of the characteristic mineral regions and a corresponding centroid of each of the corresponding regions are determined, and the size of the energy spectrum mineral distribution image is calibrated according to the centroid and the corresponding centroid, to obtain a size-calibrated mineral distribution image.

Step S14 specifically includes:

1) A first centroid, a second centroid, a third centroid, a first corresponding centroid, a second corresponding centroid, and a third corresponding centroid are calculated, wherein the first centroid is a centroid of a first characteristic mineral region, the second centroid is a centroid of a second characteristic mineral region, the third centroid is a centroid of a third characteristic mineral region, the first corresponding centroid is a centroid of a region corresponding to the first characteristic mineral region, the second corresponding centroid is a centroid of a region corresponding to the second characteristic mineral region, and the third corresponding centroid is a centroid of a region corresponding to the third characteristic mineral region.

2) A first triangle centroid and a second triangle centroid are calculated, wherein the first triangle centroid is a centroid of a triangle formed by the first centroid, the second centroid, and the third centroid, and the second triangle centroid is a centroid of a triangle formed by the first corresponding centroid, the second corresponding centroid, and the third corresponding centroid.

3) A first slope, a first vertical distance, and a first horizontal distance are calculated according to the first centroid, the second centroid, the third centroid, and the first triangle centroid, wherein the first slope is a slope of a connecting line between the first triangle centroid and the first centroid, the first vertical distance is a vertical distance from the first triangle centroid to the first centroid, and the first horizontal distance is a horizontal distance from the second centroid to the third centroid.

4) A second slope, a second vertical distance, and a second horizontal distance are calculated according to the first corresponding centroid, the second corresponding centroid, the third corresponding centroid, and the second triangle centroid, wherein the second slope is a slope of a connecting line between the second triangle centroid and the first corresponding centroid, the second vertical distance is a vertical distance from the second triangle centroid to the first corresponding centroid, and the second horizontal distance is a horizontal distance from the second corresponding centroid to the third corresponding centroid.

5) The energy spectrum mineral distribution image is rotated such that a second slope corresponding to the energy spectrum mineral distribution image is converted into the first slope to obtain a rotated energy spectrum mineral distribution image.

6) The rotated energy spectrum mineral distribution image are enlarged m times in the X-axis direction and n times in the Y-axis direction to obtain an enlarged energy spectrum mineral distribution image, wherein m is a ratio of the first horizontal distance to the second horizontal distance, and n is a ratio of the first vertical distance to the second vertical distance.

7) The enlarged energy spectrum mineral distribution image and the mud shale SEM gray-scale image are superimposed, an overlapped region of the enlarged energy spectrum mineral distribution image with the mud shale SEM gray-scale image is retained, and the overlapped region is determined as a size-calibrated mineral distribution image.

Step S15: corrosion image processing is performed on the size-calibrated mineral distribution image. Specifically, corrosion image processing is performed on each type of mineral particles in the size-calibrated mineral distribution image to obtain an image of the corroded particles.

Step S16: a segmented mud shale SEM gray-scale image is obtained by using a watershed algorithm. Specifically, the image of the corroded particle is used as a foreground color and the inorganic mineral pore image and the kerogen region image as background colors. The mud shale SEM gray-scale image is segmented by using a watershed algorithm to obtain a segmented mud shale SEM gray-scale image. The segmented mud shale SEM gray-scale image has a plurality of independent regions.

Step S17: the number of pixel points of different mineral types is counted. Specifically, the segmented mud shale SEM gray-scale image and the size-calibrated energy spectrum mineral distribution image are superimposed, and the number of pixel points of all different mineral types in each of the independent regions is counted.

Step S18: the mineral type of the independent region is determined. Specifically, the mineral type having the maximum number of pixel points in each of the independent regions is determined as a mineral type corresponding to the independent region.

Step S19: a resolution-calibrated energy spectrum mineral distribution image is determined. Specifically, resolution calibration is performed on the size-calibrated energy spectrum mineral distribution image according to all the independent regions with the mineral type determined, to obtain a resolution-calibrated energy spectrum mineral distribution image.

Embodiment 2

Figure 2:
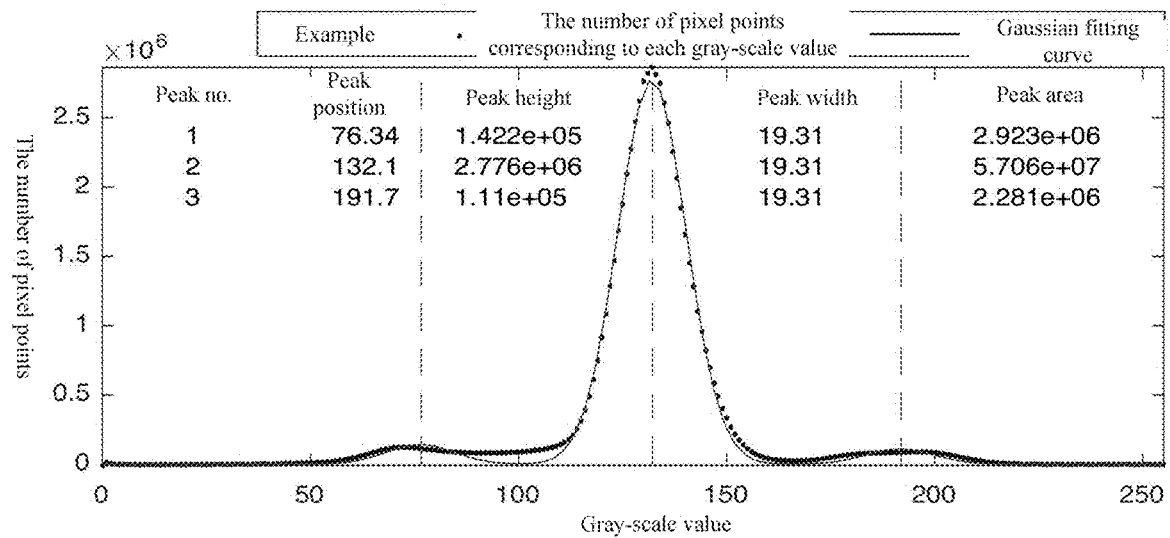
FIG. 2 is a schematic diagram of a relationship curve and a fitting curve according to Embodiment 2 of the present invention.

In this embodiment, an automatic identification method for different types of pores of mud shale includes:

Step 1: a mud shale SEM gray-scale image is obtained by using an SEM, and an energy spectrum distribution image corresponding to the mud shale SEM gray-scale image is obtained by an EDS. The mud shale SEM image is converted into an 8-bit gray-scale image, and the number of pixel points in each gray scale from 0 to 255 in the mud shale SEM gray-scale image is counted, and the relationship curve of the number of pixel points is changed with the gray scale. As shown in FIG. 2, in the relationship curve composed of a plurality of points, each scatter represents the number of pixel points corresponding to a gray-scale value.

Step 2: the Gaussian peak-differentiating and fitting method is used to fit the relationship curve obtained in step 1, to obtain a fitting curve, and the organic matter peak (Peak1), the main mineral peak (Peak2) and the bright mineral peak (Peak3) can be determined by the fitting curve. The gray-scale values corresponding to the highest values of the organic matter peak, the main mineral peak and the bright mineral peak are found and recorded as $V_{P1}$, $V_{P2}$, and $V_{P3}$, respectively, and the peak width W is recorded. As shown in FIG. 2, $V_{P1}$=75.73, $V_{P2}$=132.5, $V_{P3}$=192, and W=18.94. The main mineral peak is a quartz-feldspar-calcite mineral peak, and the bright mineral peak is a pyrite-apatite-rutile mineral peak.

Figure 3:
FIG. 3 shows an initial pore image and an initial kerogen pore image according to Embodiment 2 of the present invention.
Figure 3:
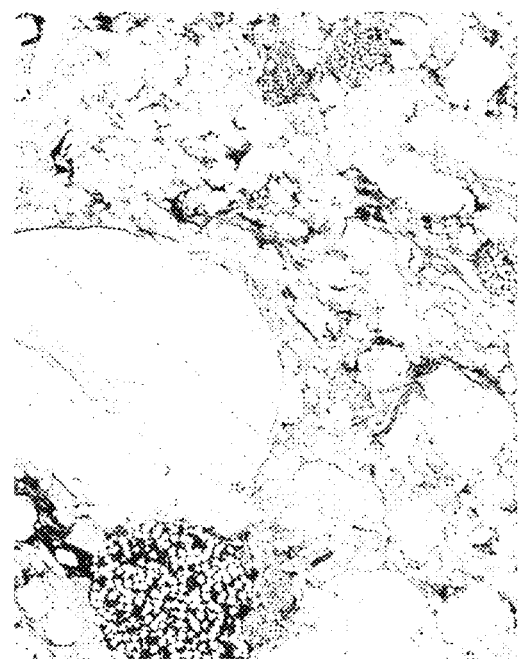

Step 3: the peak width W is subtracted from the gray-scale value $V_{P1}$ corresponding to the highest value of the organic matter peak and rounded up to obtain a first pore gray-scale cutoff value $P_{cutoff}$, and the peak width W is subtracted from the gray-scale value $V_{P2}$ corresponding to the highest value of the main mineral peak and rounded up to obtain a kerogen gray-scale cutoff value $K_{cutoff}$ ($P_{cutoff}$ is 57, and $K_{cutoff}$ is 113), and $P_{cutoff}$ and $K_{cutoff}$ are used to perform threshold segmentation on the mud shale SEM gray-scale image to obtain an initial pore image and an initial kerogen pore image. The initial pore image is a binarization image generated by assigning a value less than $P_{cutoff}$ to 0 and a value greater than $P_{cutoff}$ to 1. The initial kerogen pore image is a binarization image generated by assigning a value less than or equal to $K_{cutoff}$ to 0 and a value greater than $K_{cutoff}$ to 1. As shown in FIG. 3, part (a) in FIG. 3 is the initial pore image, and part (b) in FIG. 3 is the initial kerogen pore image.

Figure 4:
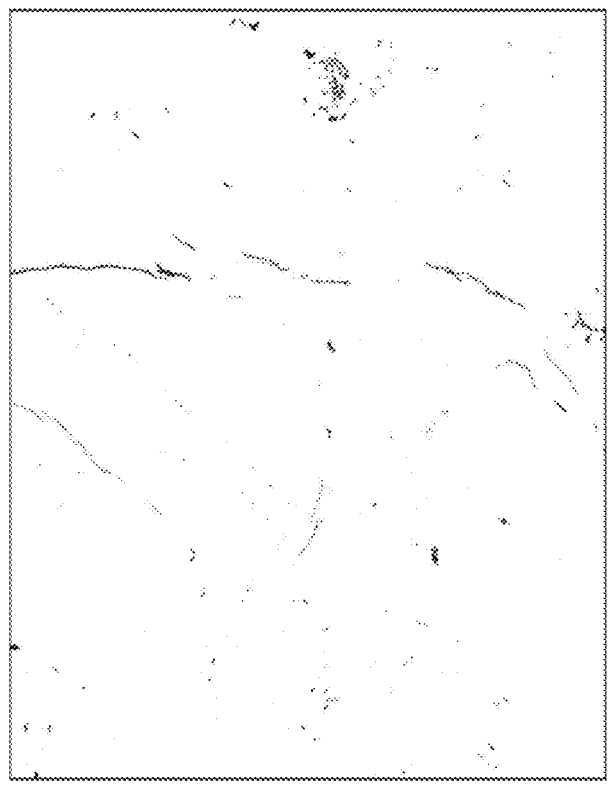
FIG. 4 shows an inorganic mineral pore image according to Embodiment 2 of the present invention.

Step 4: the initial pore image is superimposed with the initial kerogen pore image. The sum $L_{ki}$ of the outer circumference and the inner circumference of each isolated communication region in the initial kerogen pore image, the area $S_{ki}$, the long axis $L_{li}$, and the short axis $L_{si}$, as well as the area $S_{pij}$ of each pore in the initial pore image are counted. The maximum area in $S_{pij}$ is found to establish a kerogen region discriminant function $Q_{sti}=(S_{pijmax}/S_{ki})/[L_{ki}/S_{ki}/(L_{li}/L_{si})]$, and whether the isolated communication region in the initial kerogen pore image is kerogen is determined by using the kerogen region discriminant function. If the $Q_{sti}$ corresponding to the i-th isolated communication region is less than or equal to 1, the i-th isolated communication region in the initial kerogen pore image is kerogen, and if $Q_{sti}$ is greater than 1, the i-th isolated communication region is the inorganic mineral pore. By combining all the isolated communication regions with $Q_{sti}$ greater than 1, the inorganic mineral pore image can be obtained, as shown in FIG. 4.

Figure 5:
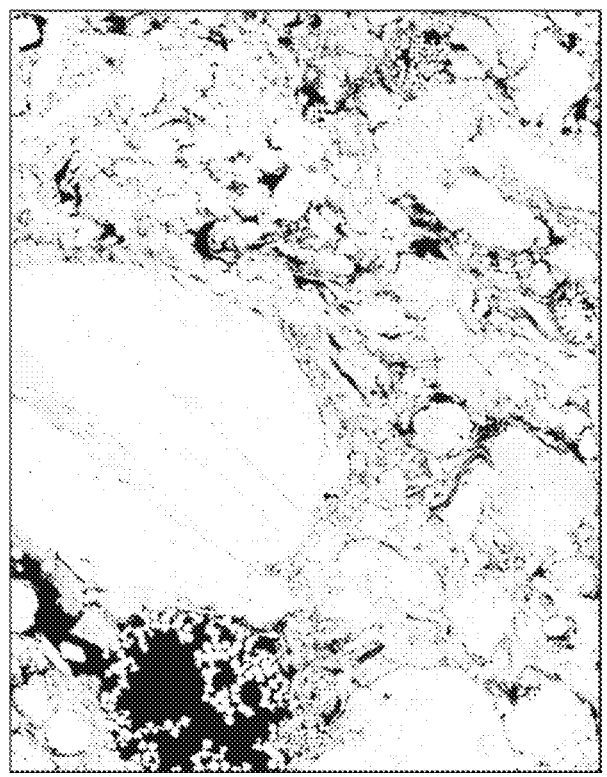
FIG. 5 shows an initial kerogen region image according to Embodiment 2 of the present invention.

Step 5: the isolated communication regions of the kerogen obtained in step 4 are combined to form a kerogen region, the kerogen region is converted into a binarization image, and inner filling is performed on the binarization image obtained after the conversion to obtain an initial kerogen region image, as shown in FIG. 5.

Figure 6:
FIG. 6 shows a bright mineral region image according to Embodiment 2 of the present invention.

Step 6: the bright mineral gray-scale cutoff value $M_{cutoff}$ ($M_{cutoff}$ is 151) is obtained by using the gray-scale value VP3 corresponding to the highest point of the bright mineral peak plus the peak width W and rounding, and threshold segmentation is performed on the mud shale SEM gray-scale image obtained in step 1 by using $M_{cutoff}$ to obtain a bright mineral image, as shown in FIG. 6.

Figure 7:
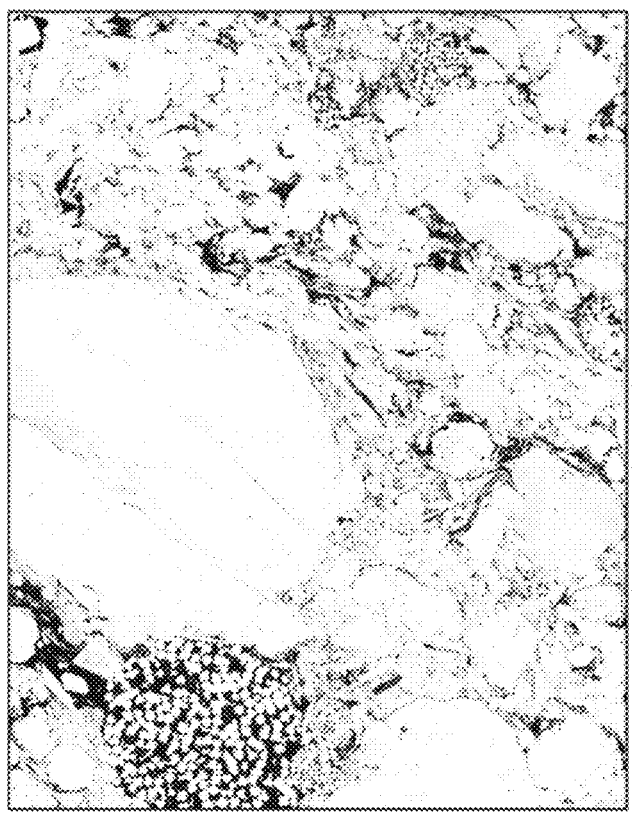
FIG. 7 shows a kerogen region image according to Embodiment 2 of the present invention.

Step 7: the initial kerogen region image obtained in step 5 is superimposed with the bright mineral image obtained in step 6, and the corresponding bright mineral region in the initial kerogen region image is deleted, and then corrosion treatment is performed to obtain a kerogen region image, as shown in FIG. 7.

Figure 8:
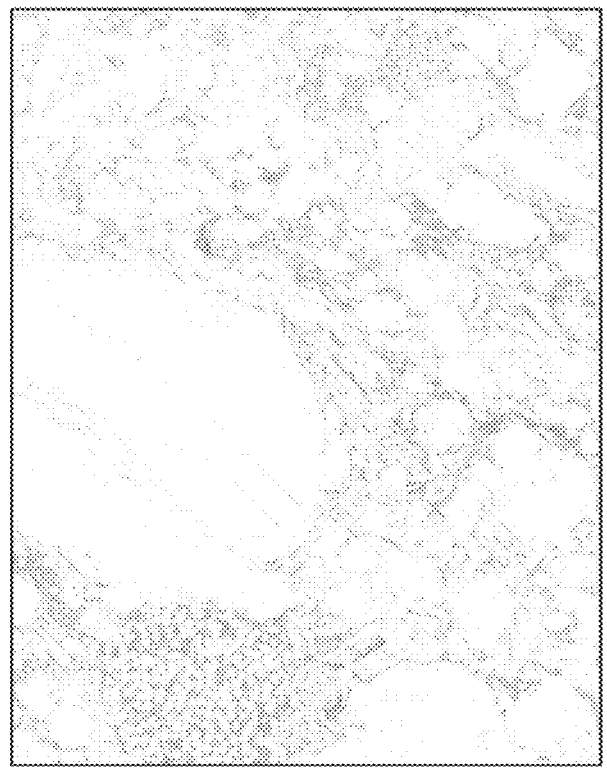
FIG. 8 shows a calibration image according to Embodiment 2 of the present invention.

Step 8: a Sobel operator, a Prewitt operator, a Roberts operator and a Canny operator are used to perform edge extraction on the mud shale SEM gray-scale image obtained in step 1, respectively, and the edge images obtained by the four operators are combined to obtain a mud shale edge extraction image. The mud shale edge extraction image is combined with the kerogen region image obtained in step 7. The edge other than the corresponding kerogen region image in the mud shale edge extraction image is deleted. The processed edge image is used as a calibration image, as shown in FIG. 8.

Figure 9:
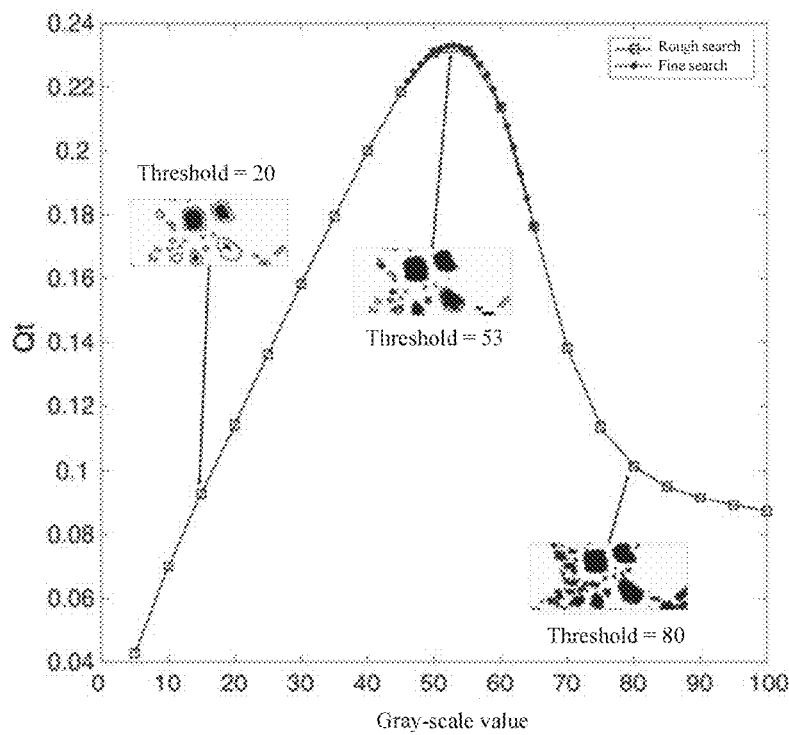
FIG. 9 is an optimal threshold discrimination diagram according to Embodiment 2 of the present invention.

Step 9: the mud shale SEM gray-scale image obtained in step 1 is subjected to image segmentation according to a preset threshold (it is started from the gray-scale value 0, every 5 gray-scale values are used as a threshold for rough searching, then every 1 gray-scale value is used as a threshold for fine searching from start (roughly searching for the optimal threshold −9) to end (roughly searching for the optimal threshold +10) after the optimal threshold in the rough searching is found) to obtain a first pore image. The first pore image is superimposed with the kerogen region image obtained in step 7. The pores other than the corresponding kerogen region in the first pore image are deleted to obtain a second pore, and the second pore is compared with the calibration image. The number of pixel points within the edge of the calibration image is recorded as $A_{inside}$. The larger the value, the better. The number of pixel points that fall outside the edge of the calibration image is recorded as $A_{outside}$, and the error function is $Q_{error}=A_{outside}/A_{inside}$. The smaller the value, the better. Balancing the two values makes the area of the pores within the edge large, and also makes the error small, and makes the discriminant function $Q_f=A_{inside}/(Q_{error})^{0.5}$. The threshold is the optimal threshold when the discriminant function is maximum, and finally the pore image under the optimal threshold can be determined. The optimal threshold discrimination process is shown in FIG. 9. It can be seen from FIG. 9 that when the threshold is 20 (the threshold is too small), although the pores (black block) in the second pore image do not fall outside the pore edge of the calibration image, the pores cannot well fill the pore edge of the calibration image. When the threshold is 80 (the threshold is too large), although the pores in the second pore image can well fill the pore edges of the calibration image, many pores fall outside the pore edge, causing a large amount of errors. When the optimal threshold is taken, the second pore image can well fill the pore edge of the calibration image, and only a few of the second pore image falls outside the pore edge, and the error is also small.

Figure 10:
FIG. 10 shows an organic pore image according to Embodiment 2 of the present invention.

Step 10: each edge of the calibration image obtained in step 8 is subjected to inner filling, and combined with the pore image at the optimal threshold obtained in step 9, to obtain the final organic pore image, as shown in FIG. 10.

Figure 11:
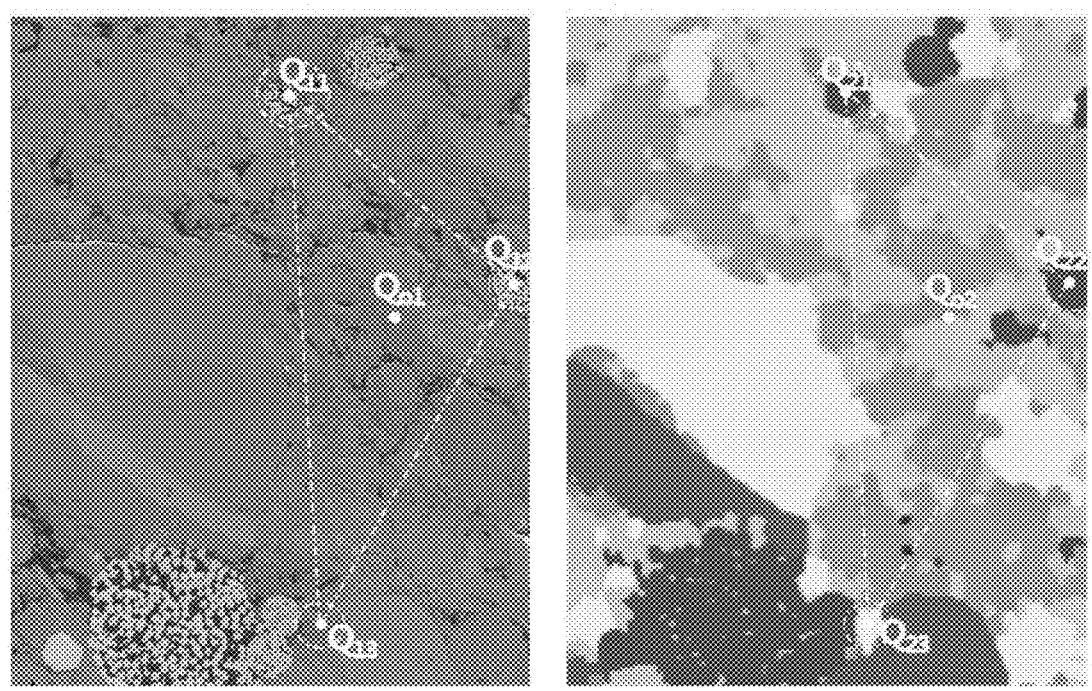
FIG. 11 shows a mud shale SEM gray-scale image and a corresponding energy spectrum mineral distribution image according to Embodiment 2 of the present invention.

Step 11: three characteristic mineral regions (such as pyrite, apatite, and drutile) on the mud shale SEM gray-scale image are determined and circled. The centroid of each characteristic mineral region is calculated, and the three centroid positions $Q_{11}(x_{11}, y_{11})$, $Q_{12}(x_{12}, y_{12})$, and $Q_{13}(x_{13}, y_{13})$ are recorded. The centroid $Q_{p1}(x_{o1}, y_{o1})$ of a triangle formed by the three centroids is calculated. The corresponding mineral position on the energy spectrum mineral image are founded and circled. The centroid of each characteristic mineral region is calculated, the three centroid positions $Q_{21}(x_{21}, y_{21})$, $Q_{22}(x_{22}, y_{22})$, and $Q_{23}(x_{23}, y_{23})$ are recorded, and the centroid $Q_{o2}(x_{o2}, y_{o2})$ of a triangle formed by the three centroids is calculated, as shown in FIG. 11. The slope $k_1$ and the vertical distance $y_{o1-11}$ (subtracting $y_{o1}$ from $y_{11}$) of the centroid $Q_{o1}$ to the centroid $Q_{11}$ in the mud shale SEM gray-scale image are calculated, and the horizontal distance $x_{12-13}$ of the centroid $Q_{12}$ to the centroid $Q_{13}$ is calculated (subtracting $x_{12}$ from $x_{13}$). The slope $k_2$ and the vertical distance $y_{o2-21}$ (subtracting $y_{o2}$ from $y_{21}$) of the centroid $Q_{o2}$ to the centroid $Q_{21}$ in the mineral distribution image are calculated. The horizontal distance $x_{22-23}$ of the centroid $Q_{22}$ to the centroid $Q_{23}$ is calculated (subtracting $x_{22}$ from $x_{23}$). The energy spectrum mineral distribution image is rotated by θ, so that the slope $k_2$ becomes the slope $k_1$. The mineral distribution image is enlarged by $x_{12-13}/x_{22-23}$ times in the X-axis direction and by $y_{o1-11}/y_{o2-21}$ times in the Y-axis direction. The enlarged energy spectrum mineral distribution image is superimposed with the mud shale SEM gray-scale image, and the regions that cannot be overlapped in the enlarged energy spectrum mineral distribution image is cut to obtain a size-calibrated mineral distribution image.

Figure 12:
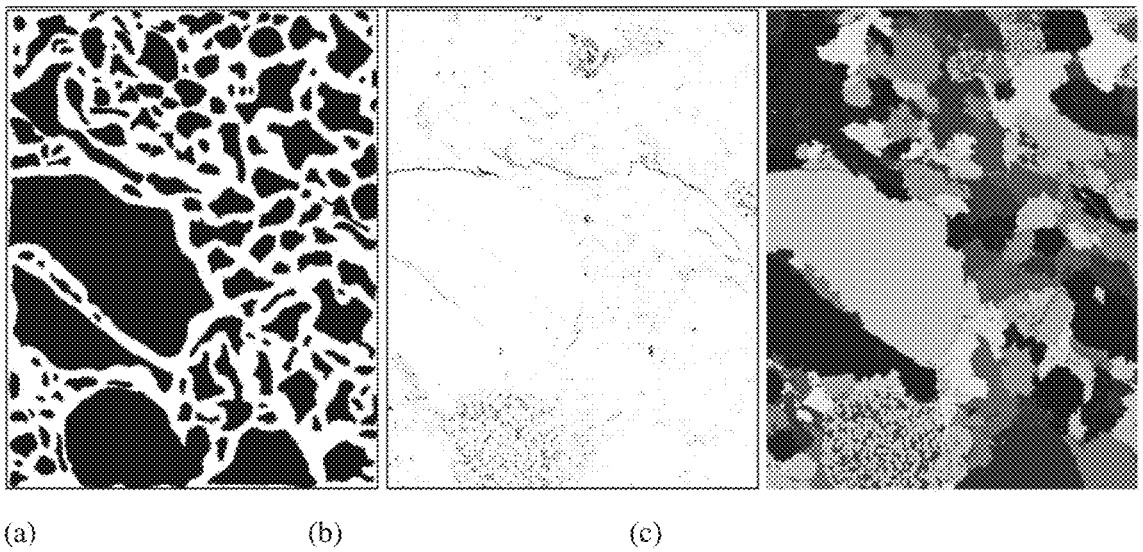
FIG. 12 shows a foreground color region image, a background color region image, and a watershed method result image according to Embodiment 2 of the present invention.

Step 12: the corrosion image operation is performed on each mineral particle in the image by using the size-calibrated mineral distribution image obtained in step 11, and the image of the corroded particle is used as the foreground color, and the foreground color region is as shown in part (a) of FIG. 12. The inorganic mineral pore image obtained in the step 4 and the kerogen region image obtained in step 7 are used as the background color, and the background color region is as shown in part (b) of FIG. 12. The SEM gray-scale image is subjected to image segmentation by a watershed method and divided into independent regions, and the watershed result image is shown in part (c) of FIG. 12.

Figure 13:
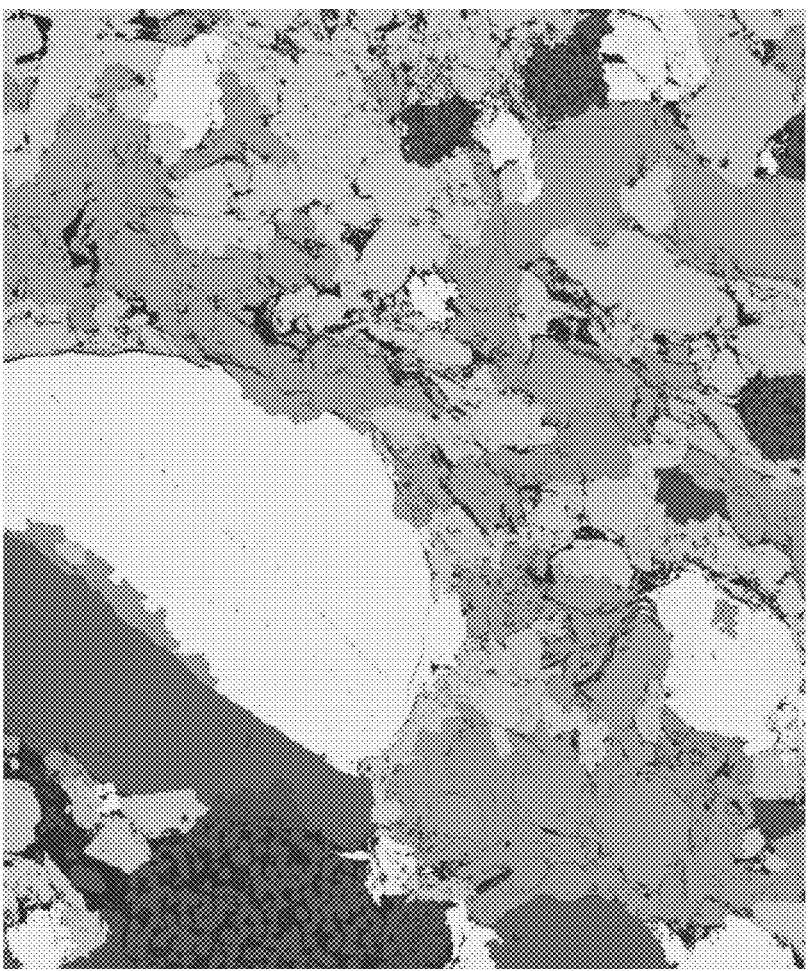
FIG. 13 shows a resolution-calibrated energy spectrum mineral distribution image according to Embodiment 2 of the present invention.

Step 13: the segmented mud shale SEM gray-scale image obtained in step 12 is superimposed with the size-calibrated mineral distribution image obtained in step 11 to calibrate the pixel positions of the two images. The number of pixel points of different types of minerals in the independent region in the divided mud shale SEM gray-scale image is counted. The independent region is named as the mineral type with the most pixel points, and finally the mineral distribution image matching the secondary electronic gray-scale image is obtained, that is, the resolution-calibrated energy spectrum mineral distribution image is shown in FIG. 13.

Step 14: an expansion operation is performed on the inorganic mineral pore image obtained in step 4, and the circle which is extra after the expansion operation is determined as an expansion region. The mineral composition ratio of the pixel points in the corresponding region of expansion is counted, and the corresponding region of expansion is a region in the resolution-calibrated energy spectrum mineral distribution image corresponding to the expansion region. Quartz, albite and potassium feldspar are classified as siliceous minerals. Calcite, dolomite and apatite are classified as calcareous minerals. Illite/smectite mixed layer, illite and chlorite are classified as clay minerals. The number of quartz pixel points $Pixel_{Si1}$, the number of albite pixel points $Pixel_{Si2}$, the number of potassium feldspar pixel points $Pixel_{Si3}$, the number of calcite pixel points $Pixel_{Ca1}$, the number of dolomite pixel points $Pixel_{Ca2}$, the number of apatite pixel points $Pixel_{Ca3}$, the number of illite/smectite mixed layer pixel points $Pixel_{C11}$, the number of illite pixel points $Pixel_{C12}$, and the number of chlorite pixel points is $Pixel_{C13}$ in the expanded circle are counted. Wherein The number of pixel points of the siliceous mineral $Pixel_{Si}=Pixel_{Si1}+Pixel_{Si2}+Pixel_{Si3}$.

The number of pixel points of the calcareous mineral $Pixel_{Ca}=Pixel_{Ca1}+Pixel_{Ca2}+Pixel_{Ca3}$.

The number of pixel points of the clay mineral $Pixel_{C1}=Pixel_{C11}+Pixel_{C12}+Pixel_{C13}$.

Figure 14:
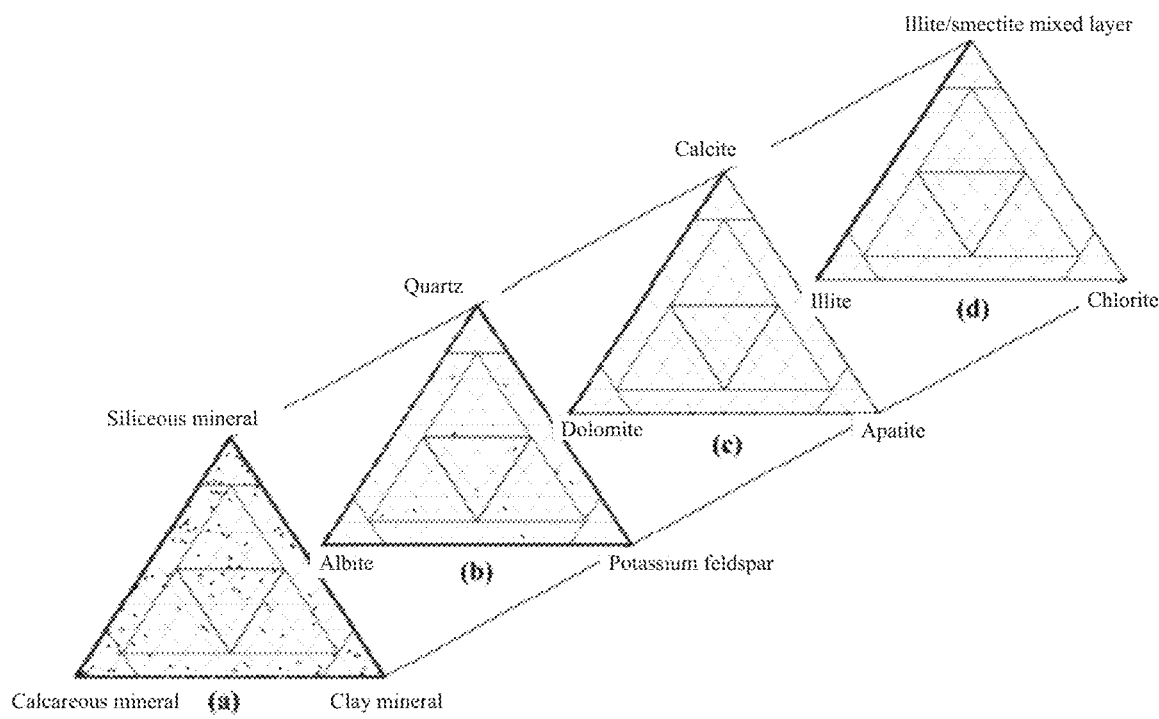
FIG. 14 is a triangular view of different types of pores according to Embodiment 2 of the present invention.
Figure 15:
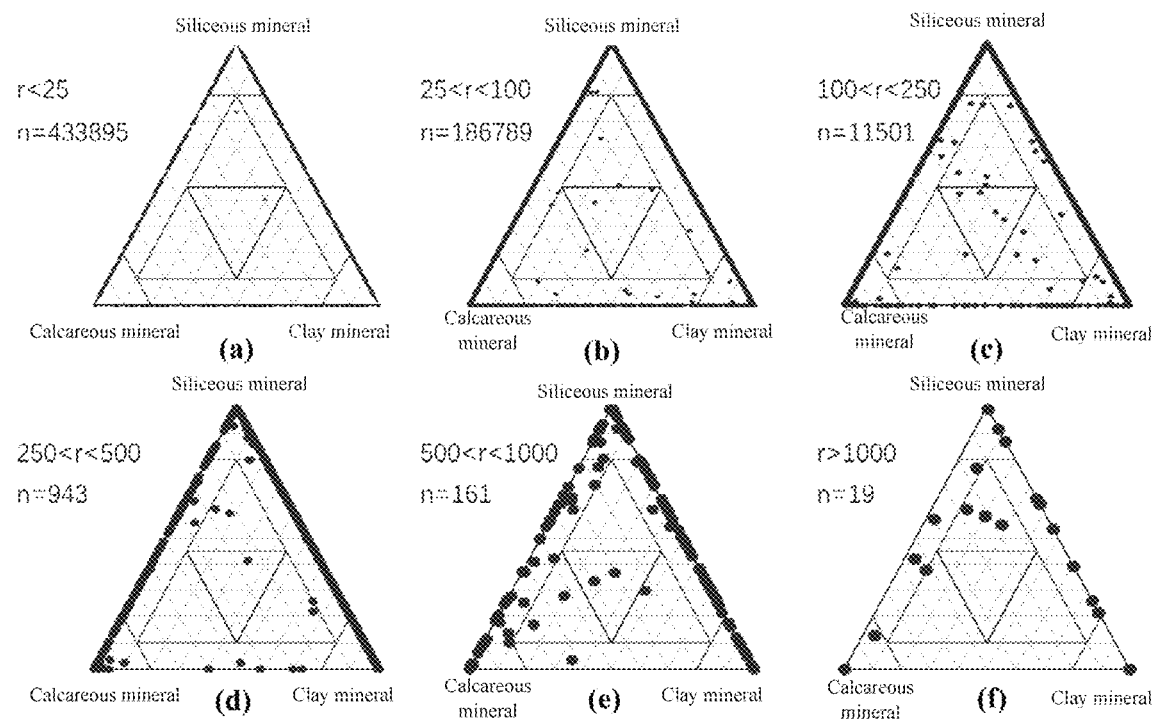
FIG. 15 is a triangular view of mineral pores of different pore sizes according to Embodiment 2 of the present invention.

The proportion of siliceous minerals is $F_{Si}=Pixel_{Si}/(Pixel_{Si}+Pixel_{Ca}+Pixel_{C1})\times 100$. Similarly, the proportion of calcium minerals $F_{Ca}$ and clay minerals $F_{C1}$ can be obtained. A mineral pore triangular image chart is drawn by setting (0,0) as the calcareous mineral end member, (50,100) as the siliceous mineral end member, and (100,0) as the clay mineral end member, and connecting every two of the end members. The respective mineral proportions of the obtained pores are converted into X, Y coordinates in a rectangular coordinate system. $X=F_{C1}+F_{Si}/2$, $Y=F_{Si}$. The pores of different mineral proportions are disposed in the mineral pore triangular image chart according to the X, Y coordinate points, so as to quantitatively evaluate which minerals control the pores, as shown in FIGS. 14 and 15. Part (a) of FIG. 14 shows a siliceous mineral-calcium mineral-clay mineral pore triangular image. Part (b) of FIG. 14 shows a quartz-albite-potassium feldspar pore triangular image when the proportion of siliceous minerals in the pores is more than 50%. Part (c) of FIG. 14 shows the calcite-dolomite-apatite pore triangular image when the proportion of calcareous minerals in the pores is greater than 50%. Part (d) of FIG. 14 shows the illite/smectite mixed layer-illite-chlorite pore triangular image when the proportion of clay minerals in the pores is greater than 50%. It can be seen from FIG. 14 that the pores are mostly controlled by a single mineral or controlled by two minerals, and less pores are controlled by three minerals and have a small proportion. Moreover, the pores controlled by quartz, albite and potassium feldspar in the pores controlled by siliceous minerals are relatively uniform. The pores of calcareous minerals are mainly controlled by calcite and dolomite, and apatite pores are less. The pores controlled by the clay minerals mainly develop the illite/smectite mixed layer pores and illite pores, and the kaolinite pores are less. Part (a) of FIG. 15 shows a mineral pore triangular image with a pore size of less than 25 nm, where r represents the pore size, and n represents the number of pores. Part (b) of FIG. 15 shows a mineral pore triangular image with a pore size ranging from 25 nm to 100 nm. Part (c) of FIG. 15 shows a mineral pore triangular image with a pore size ranging from 100 nm to 250 nm. Part (d) of FIG. 15 shows a mineral pore triangular image with a pore size ranging from 250 nm to 500 nm. Part (e) of FIG. 15 shows a mineral pore triangular image with a pore size ranging from 500 nm to 1,000 nm. Part (f) of FIG. 15 shows a mineral pore triangular image with a pore size greater than 1,000 nm. It can be seen from FIG. 15 that the pores in the range of less than 25 nm, 25-100 nm, and 100-200 nm are mainly calcareous mineral-siliceous mineral pores and siliceous mineral-clay mineral pores, and the calcareous mineral-clay mineral pores are less. The pores in the range of 250-500 nm and 500-1,000 nm are mainly calcareous minerals-siliceous mineral pores and siliceous mineral-clay mineral pores, and calcareous mineral-clay mineral pores are scarce. The pores >1000 nm are mainly siliceous mineral-clay mineral pores, the siliceous mineral-calcium mineral pores are less, and calcareous mineral-clay mineral pores are scarce.

The automatic identification method for different types of pores of mud shale of this embodiment can quantitatively identify which minerals control the pores. Compared with the previous mode of artificially superimposing the mineral distribution image and the SEM gray-scale image to obtain different mineral pore images, the method improves the identification accuracy and efficiency. Segmenting the organic pores and inorganic pores in the mud shale SEM gray-scale image by using a discriminant function simplifies the conventional method of identifying the organic pores and inorganic pores by using the mineral distribution image obtained by EDS spectrum and realizes calibration of the energy spectrum mineral distribution image.

During identification of the pores of different minerals, compared with the existing method of artificially superimposing the energy spectrum mineral distribution image obtained by the EDS with the SEM gray-scale image to obtain different mineral pore images, this embodiment increases the image resolution after resolution calibration by 1-2 orders of magnitude, and overcomes the problem that the edges of the energy spectrum mineral image are zigzag-shaped, thus improving the accuracy of identification of different types of pores.

The SEM image is pre-processed in steps 1 and 2, which overcomes the problems of threshold method, the edge extraction method and the watershed method. In the threshold method, it is easy to identify kerogen and dark mineral region as pores due to the presence of kerogen and dark minerals in shale, causing errors (regional threshold extraction is also carried out). Moreover, the internal brightness of some shallower large holes is higher, the overall color is brighter. The internal brightness of the large holes with uneven interior is different, and thus it is easy to ignore these bright regions to cause errors. In the edge extraction method, the uneven surface (edge angle) of the sample and the edges of the contaminants caused by the edge of the kerogen, the edge of the mineral, and the sample pretreatment process will be extracted, resulting in a lot of errors. Moreover, during the extraction of shallow holes, and inclined angular pores, the edges may not be fully filled, and the pores may not be filled during the filling of the pores, resulting in errors. The problem of the watershed method is similar to the edge extraction method. The kerogen, minerals, pretreatment, and pollutants would cause a lot of errors. Moreover, the watershed method divides the large holes of different internal roughness into different small pores, which causes a lot of errors. The identification accuracy is improved.

The threshold is automatically obtained in steps 3-5, and the pores obtained by the edge extraction method are combined with the pores obtained by the optimal threshold, which greatly improves the accuracy of automatic pore identification.

The inorganic mineral pores obtained in steps 1-4 are larger than the inorganic pores in the pores obtained by uniform threshold segmentation, and the accuracy is high, which is more in line with the actual situation.

Segmentation is performed on the kerogen region of the SEM image in steps 5-7, which also overcomes the problems of the threshold method, the edge extraction method and the watershed method, and improves the identification accuracy.

The threshold is automatically obtained in steps 8-10, and the pores obtained by the edge extraction method are combined with the pores obtained by the optimal threshold, which greatly improves the accuracy of automatic pore identification.

The resolution of the mineral distribution image and the resolution of the SEM gray-scale image are calibrated in steps 11-13, which solves the problem of low resolution of the energy spectrum mineral distribution image.

Different types of pores are automatically obtained in step 14, which greatly improves the accuracy and efficiency of the previous mode of artificially superimposing the mineral distribution image and the SEM gray-scale image to obtain different mineral pore images.

Embodiment 3

Figure 16:
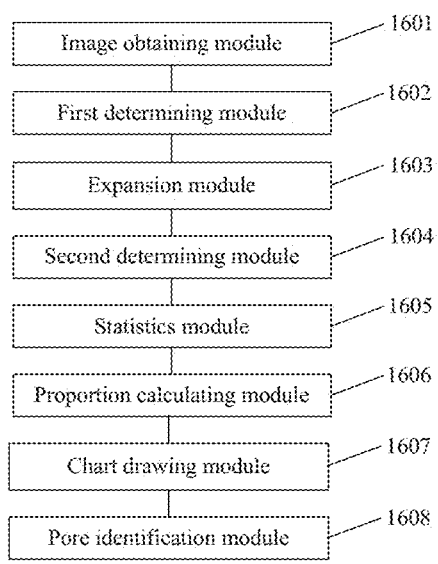
FIG. 16 is a schematic structural diagram of an automatic identification system for different types of pores of mud shale according to Embodiment 3 of the present invention.

The present invention also provides an automatic identification system for different types of pores of mud shale. FIG. 16 is a schematic structural diagram of an automatic identification system for different types of pores of mud shale according to Embodiment 3 of the present invention. Referring to FIG. 1, the automatic identification system for different types of pores of mud shale includes:

an image obtaining module 1601 configured to obtain a mud shale SEM grayscale image;

a first determining module 1602 configured to determine an inorganic mineral pore image and a kerogen region image of the mud shale SEM grayscale image;

an expansion module 1603 configured to perform an expansion operation on the inorganic mineral pore image to obtain an expanded inorganic mineral pore image;

a second determining module 1604 configured to compare the inorganic mineral pore image with the expanded inorganic mineral pore image, and determine an extra region in the expanded inorganic mineral pore image as an expansion region;

a statistics module 1605 configured to collect statistics about the number of pixel points of a siliceous mineral, the number of pixel points of a calcareous mineral, and the number of pixel points of a clay mineral in a corresponding region of expansion, the corresponding region of expansion being a region in a resolution-calibrated energy spectrum mineral distribution image corresponding to the expansion region;

a proportion calculating module 1606 configured to calculate the proportion of the siliceous mineral, the proportion of the calcareous mineral, and the proportion of the clay mineral according to the number of pixel points of the siliceous mineral, the number of pixel points of the calcareous mineral, and the number of pixel points of the clay mineral;

a chart drawing module 1607 configured to draw a mineral pore triangular image chart according to the proportion of the siliceous mineral, the proportion of the calcareous mineral, and the proportion of the clay mineral, the mineral pore triangular image chart being formed by using the siliceous mineral, the calcareous mineral, and the clay mineral as three end members, and connecting every two of the end members; and a pore identification module 1608 configured to determine the mineral type corresponding to the pores in the inorganic mineral pore image according to the mineral pore triangular image chart.

The automatic identification system for different types of pores of mud shale of this embodiment can quantitatively identify which minerals control the pores. Compared with the previous mode of artificially superimposing the mineral distribution image and the SEM gray-scale image to obtain different mineral pore images, the system improves the identification accuracy and efficiency, simplifies the conventional method of identifying the organic pores and inorganic pores by using the mineral distribution image obtained by EDS spectrum and realizes calibration of the energy spectrum mineral distribution image.

During identification of the pores of different minerals, compared with the existing method of artificially superimposing the energy spectrum mineral distribution image obtained by the EDS with the SEM gray-scale image to obtain different mineral pore images, this embodiment can improve the accuracy of identification of different types of pores.

For the system disclosed in Embodiment 3, since it corresponds to the method disclosed in Embodiment 1 or 2, the description is relatively simple, and reference can be made to the method description.

Several examples are used for illustration of the principles and implementation methods of the present invention. The description of the embodiments is used to help illustrate the method and its core principles of the present invention. In addition, those skilled in the art can make various modifications in terms of specific embodiments and scope of application in accordance with the teachings of the present invention. In conclusion, the content of this specification shall not be construed as a limitation to the present invention.

What is claimed is:

1. An automatic identification method for different types of pores of mud shale, comprising:
   obtaining a mud shale Scanning Electron Microscopy (SEM) gray-scale image;
   determining an inorganic mineral pore image and a kerogen region image of the mud shale SEM gray-scale image;
   performing an expansion operation on the inorganic mineral pore image to obtain an expanded inorganic mineral pore image;
   comparing the inorganic mineral pore image with the expanded inorganic mineral pore image, and determining an extra region in the expanded inorganic mineral pore image as an expansion region;
   collecting statistics about the number of pixel points of a siliceous mineral, the number of pixel points of a calcareous mineral, and the number of pixel points of a clay mineral in a corresponding region of expansion, the corresponding region of expansion being a region in a resolution-calibrated energy spectrum mineral distribution image corresponding to the expansion region;
   calculating the proportion of the siliceous mineral, the proportion of the calcareous mineral, and the proportion of the clay mineral according to the number of pixel points of the siliceous mineral, the number of pixel points of the calcareous mineral, and the number of pixel points of the clay mineral;
   drawing a mineral pore triangular image chart according to the proportion of the siliceous mineral, the proportion of the calcareous mineral, and the proportion of the clay mineral, the mineral pore triangular image chart being formed by using the siliceous mineral, the calcareous mineral, and the clay mineral as three end members, and connecting every two of the end members; and
   determining the mineral type corresponding to the pores in the inorganic mineral pore image according to the mineral pore triangular image chart;
   wherein the determining the inorganic mineral pore image and the kerogen region image of the mud shale SEM gray-scale image specifically comprises:
   collecting statistics about the number of pixel points of each gray-scale value in the mud shale SEM gray-scale image, and obtaining a relationship curve of the number of pixel points and the gray-scale value;
   determining a gray-scale value corresponding to the highest point of an organic matter peak, a gray-scale value corresponding to the highest point of a main mineral peak, a gray-scale value corresponding to the highest point of a bright mineral peak, and peak widths in the relationship curve, the peak widths of the organic matter peak, the main mineral peak and the bright mineral peak being the same;
   calculating a first pore gray-scale cutoff value, a kerogen gray-scale cutoff value, and a bright mineral gray-scale cutoff value by using the gray-scale value corresponding to the highest point of the organic matter peak, the gray-scale value corresponding to the highest point of the main mineral peak, the gray-scale value corresponding to the highest point of the bright mineral peak, and the peak widths;
   using the first pore gray-scale cutoff value, the kerogen gray-scale cutoff value, and the bright mineral gray-scale cutoff value to respectively perform threshold segmentation on the mud shale SEM gray-scale image to obtain an initial pore image, an initial kerogen pore image, and a bright mineral image;
   distinguishing whether kerogen is present in the initial kerogen pore image according to the initial pore image to obtain an inorganic mineral pore image and an initial kerogen region image; and
   superimposing the initial kerogen region image with the bright mineral image, and removing the corresponding bright mineral in the initial kerogen region image to obtain a kerogen region image.

2. The automatic identification method for different types of pores of mud shale according to claim 1, wherein after the determining an inorganic mineral pore image and the kerogen region image of the mud shale SEM gray-scale image, the method further comprises:
   determining a calibration image according to the kerogen region image and a mud shale edge extraction image, the mud shale edge extraction image being obtained by performing edge extraction on the mud shale SEM gray-scale image;
   performing image segmentation on the mud shale SEM gray-scale image according to a preset threshold to obtain a first pore image; and
   determining an organic pore image according to the kerogen region image, the first pore image, and the calibration image.

3. The automatic identification method for different types of pores of mud shale according to claim 1, wherein the method for determining a resolution-calibrated energy spectrum mineral distribution image comprises:
   obtaining an energy spectrum mineral distribution image corresponding to the mud shale SEM gray-scale image, the energy spectrum mineral distribution image being obtained by using an energy disperse spectroscopy;
   determining three characteristic mineral regions of the mud shale SEM gray-scale image and corresponding regions of each of the characteristic mineral regions in the energy spectrum mineral distribution image;
   calculating a centroid of each of the characteristic mineral regions and a corresponding centroid of each of the corresponding regions, and calibrating the size of the energy spectrum mineral distribution image according to the centroid and the corresponding centroid, to obtain a size-calibrated mineral distribution image;
   performing corrosion image processing on each type of mineral particles in the size-calibrated mineral distribution image to obtain an image of the corroded particles;
   using the image of the corroded particle as a foreground color and the inorganic mineral pore image and the kerogen region image as background colors, segmenting the mud shale SEM gray-scale image by using a watershed algorithm to obtain a segmented mud shale SEM gray-scale image, the segmented mud shale SEM gray-scale image having a plurality of independent regions;

superimposing the segmented mud shale SEM gray-scale image with the size-calibrated energy spectrum mineral distribution image, and collecting statistics about the number of pixel points of all different mineral types in each of the independent regions;

determining the mineral type having the maximum number of pixel points in each of the independent regions as a mineral type corresponding to the independent region; and performing resolution calibration on the size-calibrated energy spectrum mineral distribution image according to all the independent regions with the mineral type determined, to obtain a resolution-calibrated energy spectrum mineral distribution image.

4. The automatic identification method for different types of pores of mud shale according to claim 3, wherein the calculating a centroid of each of the characteristic mineral regions and a corresponding centroid of each of the corresponding regions, and calibrating the size of the energy spectrum mineral distribution image according to the centroid and the corresponding centroid, to obtain a size-calibrated mineral distribution image specifically comprises:

calculating a first centroid, a second centroid, a third centroid, a first corresponding centroid, a second corresponding centroid, and a third corresponding centroid, wherein the first centroid is a centroid of a first characteristic mineral region, the second centroid is a centroid of a second characteristic mineral region, the third centroid is a centroid of a third characteristic mineral region, the first corresponding centroid is a centroid of a region corresponding to the first characteristic mineral region, the second corresponding centroid is a centroid of a region corresponding to the second characteristic mineral region, and the third corresponding centroid is a centroid of a region corresponding to the third characteristic mineral region;

calculating a first triangle centroid and a second triangle centroid, wherein the first triangle centroid is a centroid of a triangle formed by the first centroid, the second centroid, and the third centroid, and the second triangle centroid is a centroid of a triangle formed by the first corresponding centroid, the second corresponding centroid, and the third corresponding centroid;

calculating a first slope, a first vertical distance, and a first horizontal distance according to the first centroid, the second centroid, the third centroid, and the first triangle centroid, wherein the first slope is a slope of a connecting line between the first triangle centroid and the first centroid, the first vertical distance is a vertical distance from the first triangle centroid to the first centroid, and the first horizontal distance is a horizontal distance from the second centroid to the third centroid;

calculating a second slope, a second vertical distance, and a second horizontal distance according to the first corresponding centroid, the second corresponding centroid, the third corresponding centroid, and the second triangle centroid, wherein the second slope is a slope of a connecting line between the second triangle centroid and the first corresponding centroid, the second vertical distance is a vertical distance from the second triangle centroid to the first corresponding centroid, and the second horizontal distance is a horizontal distance from the second corresponding centroid to the third corresponding centroid;

rotating the energy spectrum mineral distribution image such that a second slope corresponding to the energy spectrum mineral distribution image is converted into the first slope to obtain a rotated energy spectrum mineral distribution image;

enlarging the rotated energy spectrum mineral distribution image m times in the X-axis direction and n times in the Y-axis direction to obtain an enlarged energy spectrum mineral distribution image, wherein m is a ratio of the first horizontal distance to the second horizontal distance, and n is a ratio of the first vertical distance to the second vertical distance; and superimposing the enlarged energy spectrum mineral distribution image with the mud shale SEM gray-scale image, retaining an overlapped region of the enlarged energy spectrum mineral distribution image with the mud shale SEM gray-scale image, and determining the overlapped region as a size-calibrated mineral distribution image.

5. The automatic identification method for different types of pores of mud shale according to claim 1, wherein the determining a gray-scale value corresponding to the highest point of an organic matter peak, a gray-scale value corresponding to the highest point of a main mineral peak, a gray-scale value corresponding to the highest point of a bright mineral peak, and peak widths in the relationship curve specifically comprises:

fitting the relationship curve by using a Gaussian peak-differentiating and fitting method to obtain a fitting curve;

determining an organic matter peak, a main mineral peak, and a bright mineral peak according to the fitting curve, the main mineral peak being a quartz-feldspar-calcite mineral peak; and determining a gray-scale value corresponding to the highest point of the organic matter peak, a gray-scale value corresponding to the highest point of the main mineral peak, a gray-scale value corresponding to the bright mineral peak, and peak widths, the peak widths of the organic matter peak, the main mineral peak, and the bright mineral peak being the same.

6. The automatic identification method for different types of pores of mud shale according to claim 1, wherein the distinguishing whether kerogen is present in the initial kerogen pore image according to the initial pore image to obtain an inorganic mineral pore image and an initial kerogen region image specifically comprises:

superimposing the initial pore image and the initial kerogen pore image, and collecting statistics about a first parameter corresponding to each isolated communication region in the initial kerogen pore image and a second parameter corresponding to each pore in the initial pore image, the first parameter comprising a sum of an inner circumference and an outer circumference of the isolated communication region, the area, a long axis value, and a short axis value; and the second parameter being the area of the pores;

determining the area of the maximum pore in the initial pore image according to the second parameter;

establishing a kerogen region discriminant function according to the first parameter and the area of the maximum pore;

distinguishing whether kerogen is present in the initial kerogen pore image by using the kerogen region discriminant function to obtain an inorganic mineral pore image and a kerogen region; and filling the kerogen region to obtain an initial kerogen region image.

7. The automatic identification method for different types of pores of mud shale according to claim 2, wherein the determining a calibration image according to the kerogen region image and a mud shale edge extraction image specifically comprises:

using a Sobel operator, a Prewitt operator, a Roberts operator, and a Canny operator to perform edge extraction on the mud shale SEM gray-scale image respectively to obtain a first operator edge image, a second operator edge image, a third operator edge image, and a fourth operator edge image;

combining the first operator edge image, the second operator edge image, the third operator edge image, and the fourth operator edge image to obtain a mud shale edge extraction image; and combining the kerogen region image with the mud shale edge extraction image, and deleting the edge other than the corresponding kerogen region image in the mud shale edge extraction image to obtain a calibration image.

8. The automatic identification method for different types of pores of mud shale according to claim 2, wherein the determining an organic pore image according to the kerogen region image, the first pore image, and the calibration image specifically comprises:

superimposing the first pore image and the kerogen region image, and deleting pores other than the corresponding kerogen region image in the first pore image to obtain a second pore image;

comparing the second pore image with the calibration image to determine a pore image at an optimal threshold;

performing inner filling on edges in the calibration image to obtain a filled calibration image; and combining the filled calibration image with the pore image at the optimal threshold to obtain an organic pore image.

9. An automatic identification system for different types of pores of mud shale, comprising a processor, wherein the processor is configured to:

obtain a mud shale Scanning Electron Microscopy (SEM) gray-scale image;

determine an inorganic mineral pore image and a kerogen region image of the mud shale SEM gray-scale image;

collect statistics about the number of pixel points of each gray-scale value in the mud shale SEM gray-scale image, and obtaining a relationship curve of the number of pixel points and the gray-scale value;

determine a gray-scale value corresponding to the highest point of an organic matter peak, a gray-scale value corresponding to the highest point of a main mineral peak, a gray-scale value corresponding to the highest point of a bright mineral peak, and peak widths in the relationship curve, the peak widths of the organic matter peak, the main mineral peak and the bright mineral peak being the same;

calculate a first pore gray-scale cutoff value, a kerogen gray-scale cutoff value, and a bright mineral gray-scale cutoff value by using the gray-scale value corresponding to the highest point of the organic matter peak, the gray-scale value corresponding to the highest point of the main mineral peak, the gray-scale value corresponding to the highest point of the bright mineral peak, and the peak widths;

use the first pore gray-scale cutoff value, the kerogen gray-scale cutoff value, and the bright mineral gray-scale cutoff value to respectively perform threshold segmentation on the mud shale SEM gray-scale image to obtain an initial pore image, an initial kerogen pore image, and a bright mineral image;

distinguish whether kerogen is present in the initial kerogen pore image according to the initial pore image to obtain an inorganic mineral pore image and an initial kerogen region image; and superimpose the initial kerogen region image with the bright mineral image, and removing the corresponding bright mineral in the initial kerogen region image to obtain a kerogen region image;

perform an expansion operation on the inorganic mineral pore image to obtain an expanded inorganic mineral pore image;

compare the inorganic mineral pore image with the expanded inorganic mineral pore image, and determine an extra region in the expanded inorganic mineral pore image as an expansion region;

collect statistics about the number of pixel points of a siliceous mineral, the number of pixel points of a calcareous mineral, and the number of pixel points of a clay mineral in a corresponding region of expansion, the corresponding region of expansion being a region in a resolution-calibrated energy spectrum mineral distribution image corresponding to the expansion region;

calculate the proportion of the siliceous mineral, the proportion of the calcareous mineral, and the proportion of the clay mineral according to the number of pixel points of the siliceous mineral, the number of pixel points of the calcareous mineral, and the number of pixel points of the clay mineral;

draw a mineral pore triangular image chart according to the proportion of the siliceous mineral, the proportion of the calcareous mineral, and the proportion of the clay mineral, the mineral pore triangular image chart being formed by using the siliceous mineral, the calcareous mineral, and the clay mineral as three end members, and connecting every two of the end members; and determine the mineral type corresponding to the pores in the inorganic mineral pore image according to the mineral pore triangular image chart.

\* \* \* \* \*